United States Patent
Tsai et al.

(10) Patent No.: US 10,617,660 B2
(45) Date of Patent: Apr. 14, 2020

(54) COMPOSITIONS CONTAINING BENZOATE COMPOUND AND TANNIC ACID FOR TREATING CENTRAL NERVOUS SYSTEM DISORDERS

(71) Applicant: SyneuRx International (Taiwan) Corp., New Taipei (TW)

(72) Inventors: Guochuan Emil Tsai, Pasadena, CA (US); Ching-Hsun Huang, Taipei (TW); Ching-Cheng Wang, New Taipei (TW); Tien-Lan Hsieh, New Taipei (TW)

(73) Assignee: SyneuRx International (Taiwan) Corp., New Taipei (TW)

(*) Notice: Subject to any disclaimer, the term of this patent is extended or adjusted under 35 U.S.C. 154(b) by 0 days.

(21) Appl. No.: 16/119,439

(22) Filed: Aug. 31, 2018

(65) Prior Publication Data
US 2019/0060263 A1    Feb. 28, 2019

Related U.S. Application Data

(63) Continuation of application No. 15/655,683, filed on Jul. 20, 2017, now Pat. No. 10,064,833.

(60) Provisional application No. 62/371,081, filed on Aug. 4, 2016.

(51) Int. Cl.
| | | |
|---|---|---|
| *A61K 36/00* | (2006.01) | |
| *A61K 31/192* | (2006.01) | |
| *A61K 47/22* | (2006.01) | |
| *A61K 9/00* | (2006.01) | |
| *A61K 45/06* | (2006.01) | |
| *A61K 47/14* | (2017.01) | |

(52) U.S. Cl.
CPC .......... *A61K 31/192* (2013.01); *A61K 9/0019* (2013.01); *A61K 9/0053* (2013.01); *A61K 45/06* (2013.01); *A61K 47/14* (2013.01); *A61K 47/22* (2013.01)

(58) Field of Classification Search
None
See application file for complete search history.

(56) References Cited

U.S. PATENT DOCUMENTS

| 10,064,833 B2 | 9/2018 | Tsai et al. |
| 2007/0020332 A1* | 1/2007 | Kiel ............... A61K 9/0056 424/464 |
| 2009/0118202 A1 | 5/2009 | Thekkumkara |

FOREIGN PATENT DOCUMENTS

| CN | 102245180 A | 11/2011 |
| CN | 105079798 A | 11/2015 |

OTHER PUBLICATIONS

Khasnavis et al., Cinnamon treatment upregulates neuroprotective proteins Parkin and DJ-1 and protects dopaminergic neurons in a mouse model of Parkinson'sdisease. J Neuroimmune Pharmacol. Sep. 2014;9(4):569-81. doi:10.1007/s11481-014-9552-2. Epub Jun. 20, 2014.

* cited by examiner

*Primary Examiner* — Qiuwen Mi
(74) *Attorney, Agent, or Firm* — Polsinelli PC

(57) ABSTRACT

Compositions (e.g., pharmaceutical compositions or nutraceutical compositions) comprising a benzoate compound and an excipient, wherein the excipient is tannic acid, and uses thereof for treating central nervous system disorders.

27 Claims, 4 Drawing Sheets

COMPOSITIONS CONTAINING BENZOATE COMPOUND AND TANNIC ACID FOR TREATING CENTRAL NERVOUS SYSTEM DISORDERS

RELATED APPLICATION

This application is a continuation of U.S. patent application Ser. No. 15/655,683, filed Jul. 20, 2017, which claims the benefit of priority under 35 U.S.C. § 119(e) to U.S. Provisional Application Ser. No. 62/371,081, filed on Aug. 4, 2016, the disclosures of which are incorporated by reference herein in their entireties.

BACKGROUND OF THE INVENTION

The central nervous system (CNS) includes the brain and spinal cord. The CNS is vulnerable to various disorders, which may be caused by various factors, including trauma, infections, degeneration, structural defects and/or damages, tumors, blood flow disruption, and autoimmune disorders. Symptoms of a CNS disorder would depend on the area of the nervous system that is involved and the cause of the disorder.

The development of effective therapies for CNS disorders has lagged behind other therapeutic areas due to the complexity of such disorders and the lack of efficient technology for delivering therapeutic agents through the blood-brain barrier. As such, it is of great interest to develop new treatment approaches for CNS disorders.

SUMMARY OF THE INVENTION

The present disclosure is based, at least in part, on the unexpected discovery that tannic acid potentiated the therapeutic effects of benzoate salt on symptoms associated with CNS disorders, for example, locomotion activity and sensorimotor function as observed in a mouse model of CNS disease.

Accordingly, one aspect of the present disclosure features a composition (e.g., a pharmaceutical composition or a health food product), which comprises a benzoate compound and an excipient, wherein the excipient is single species or a mixture of multiple species of tannic acid, or a pharmaceutically acceptable salt thereof.

In some embodiments, the benzoate compound is about 100 to about 1200 mg in the composition and the tannic acid is about 2.0 to about 1200 mg in the composition. In some embodiments, the benzoate compound and the tannic acid are at a ratio of 1:100 to 100:1.

In some embodiments, any of the compositions described herein can be a pharmaceutical composition, which further comprises a pharmaceutically acceptable carrier. Any of the pharmaceutical compositions described herein may be formulated for oral administration or for parenteral administration.

In other embodiments, the composition can be a healthy food product (e.g., a nutraceutical composition, a medical food, or a health food), which may comprise an edible carrier. Such compositions may be formulated as a tablet, a capsule, a soft chew, or a gel.

In yet another aspect, the present disclosure features a method for treating a central nervous system (CNS) disorder, the method comprising administering to a subject in need thereof a therapeutically effective amount of any of the compositions described herein. In some embodiments, the therapeutically effective amount of the composition contains about 100 to about 1000 mg of the benzoate compound and about 2.5 to about 1000 mg of the tannic acid.

Exemplary CNS disorders include, but not limited to, attention deficit hyperactivity disorder (ADHD), schizophrenia, psychotic disorders, major depressive disorder, Alzheimer's disorder, pain, depressions, bipolar disorders, eating disorders, addiction disorders, personality disorders, tic disorders, post-traumatic stress disorder, anxiety disorders, social anxiety disorders, panic disorders, autism spectrum disorders, Asperger's disorder, Fragile X syndrome (FXS), obsessive-compulsive disorder (OCD), learning disorders, Tourette's syndrome, mild cognitive disorder (MCI), benign forgetfulness, closed head injury, dementia (e.g., vascular dementia, frontotemporal dementia, dementia with Lewy bodies, senile dementia, and mild dementia of Alzheimer), Parkinson's disorder, Huntington's disease, nocturnal enuresis, blepharospasm, non-epileptic seizure, premenstrual syndrome, and amyotrophic lateral sclerosis (ALS).

In some embodiments, the subject in need of treatment is a human patient having or suspected of having the CNS disorder. In some embodiments, the subject is a human patient who has been subjected to or is on another CNS disorder treatment. In some embodiments, the subject is administered with the composition at a frequency of four times a day to one time a month. In some embodiments, the composition is administered by a systemic route, which may be oral administration or parenteral administration.

Also within the scope of the present disclosure are (i) any of the compositions comprising a benzoate compound and tannic acid (e.g., pharmaceutical compositions or healthy food products) described herein for use in treating a CNS associated disease/disorder, such as those described herein, and (ii) uses of such composition in manufacturing medicaments for use in treating any of the diseases/disorders, including those described herein.

The details of one or more embodiments of the invention are set forth in the description below. Other features or advantages of the present invention will be apparent from the following drawings and detailed description of several embodiments, and also from the appended claims.

DETAILED DESCRIPTION OF THE INVENTION

The present disclosure provides compositions, kits, and methods of using such for improving basic functioning and cognitive behaviors in a subject in need of treatment, and/or for treating diseases and disorders associated with the CNS. The compositions provided by the present disclosure comprise a benzoate compound (e.g., a benzoate salt such as lithium benzoate, sodium benzoate) and an excipient, wherein the excipient is tannic acid (single species or mixture of multiple species of tannic acid), or a pharmaceutically acceptable salt thereof.

Compositions

One aspect of the present disclosure relates to compositions comprising a benzoate compound, such as sodium benzoate or lithium benzoate, and an excipient, wherein the excipient is tannic acid (single species or mixture of multiple species of tannic acid), or a pharmaceutically acceptable salt thereof. In some embodiments, the composition is a pharmaceutical composition, which further comprises a pharmaceutically acceptable carrier. In some embodiments, the composition is a nutraceutical composition, a medical food, or a health food.

Figure 2:
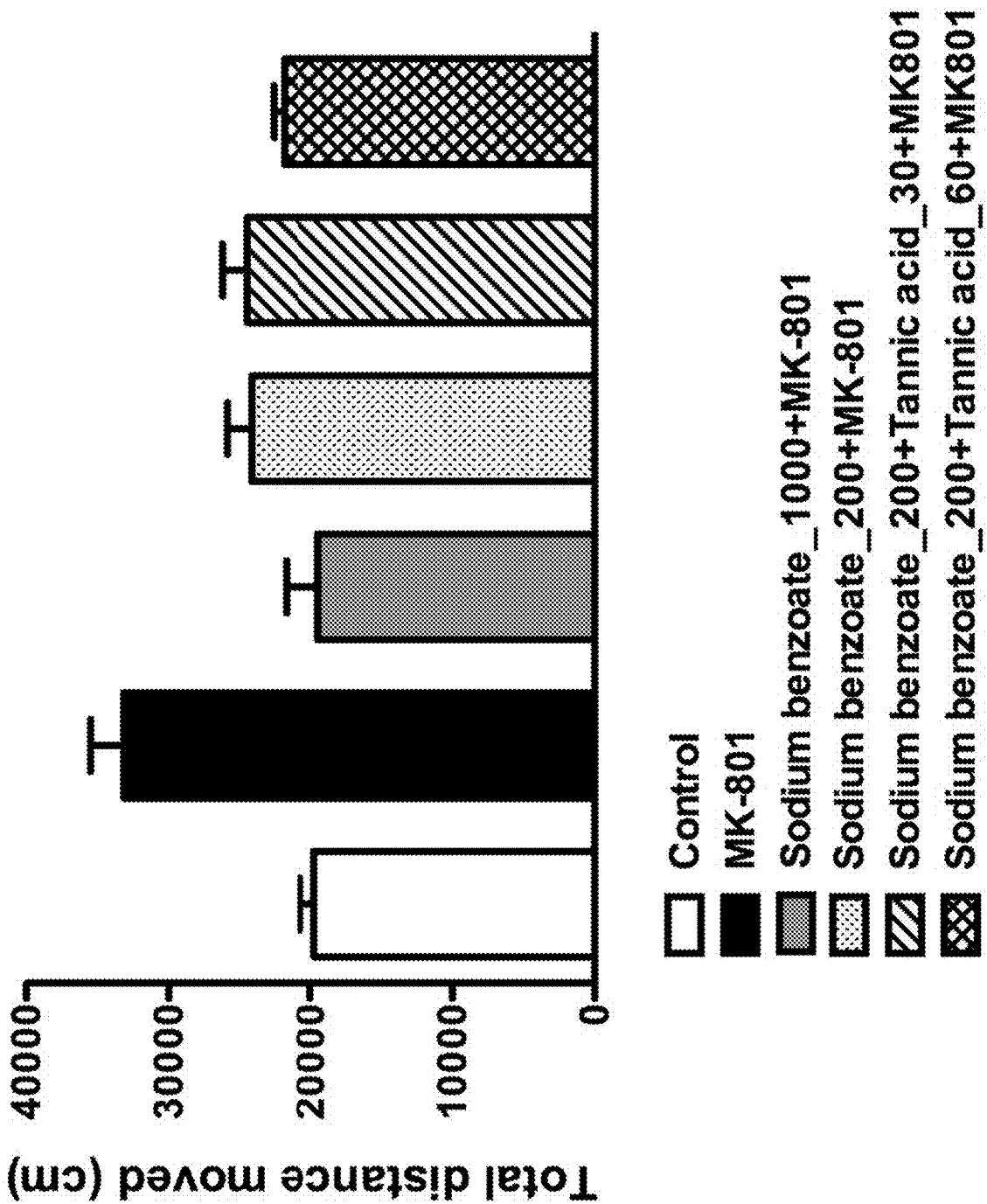
FIG. 2 is a chart showing the total distance traveled in open field test by MK801-treated mice administered sodium benzoate alone or a combination of sodium benzoate and tannic acid. MK801 induced hyperactivity, which is completely prevented by sodium benzoate at 1000 mg/kg, while 200 mg/kg of sodium benzoate is less effective. However, 60 mg/kg tannic acid improves the effects of 200 mg/kg of sodium benzoate whereas 30 mg/kg tannic acid does not.
Figure 3:
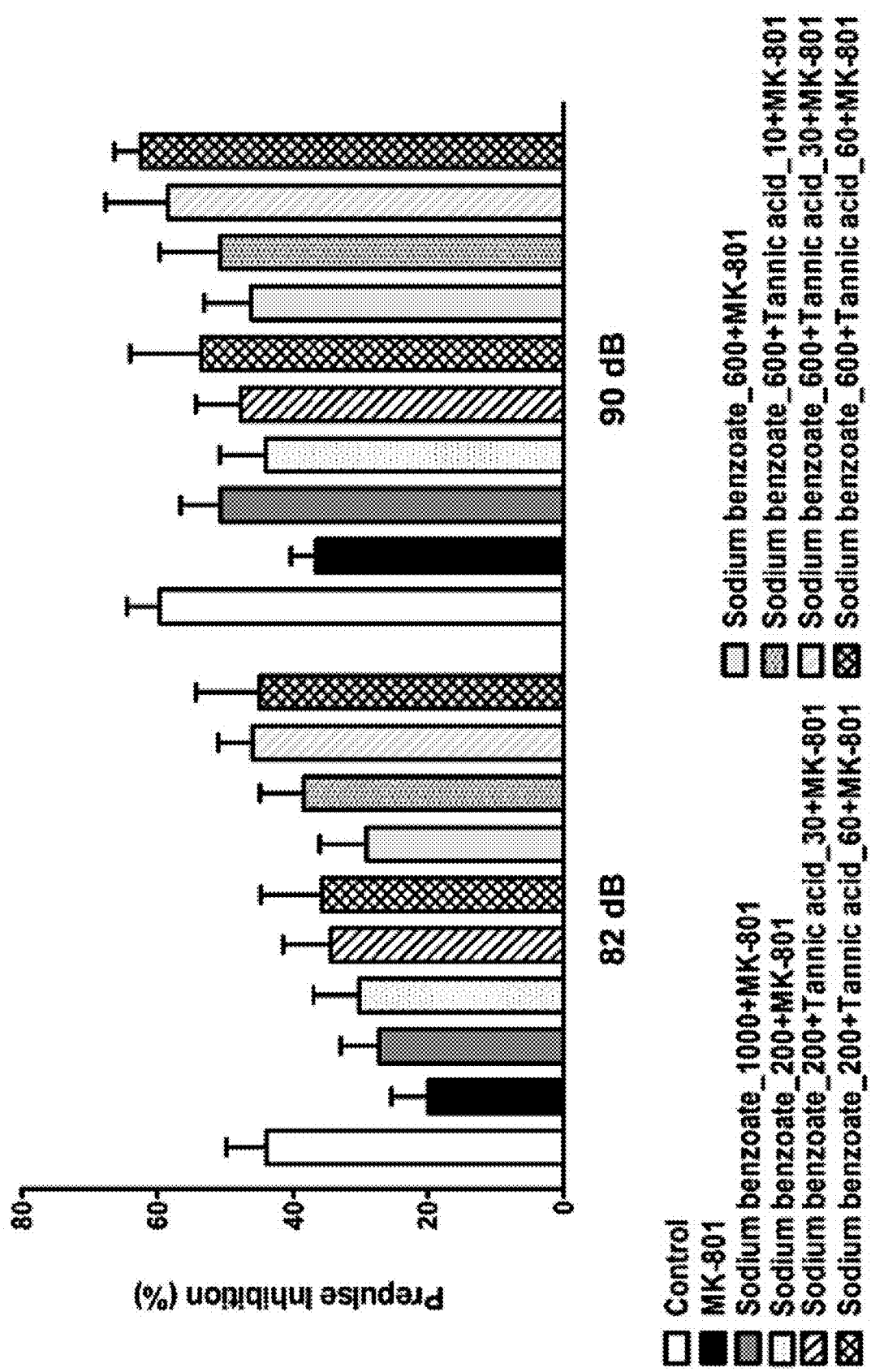
FIG. 3 is a chart showing the percentage of pre-pulse inhibition in MK801-treated mice administered sodium benzoate alone or a combination of sodium benzoate and tannic acid. MK801 impairs prepulse inhibition which can be improved by sodium benzoate at 200, 600 or 1000 mg/kg. At the same time, tannic acid dose-dependently further improves the effect of sodium benzoate on the prepulse inhibition.

The compositions of the present disclosure are useful in alleviating one or more symptoms associated with a CNS disease as described herein (e.g., hyperactivity and/or sensorimotor deficit) or for treating the target CNS disease. The examples demonstrate that tannic acid potentiates the protective effects of benzoate on symptoms of CNS diseases including locomotion activity and sensorimotor gating function. Administration of tannic acid in combination with sodium benzoate allowed a reduction in the amount of sodium benzoate that can be administered to produce therapeutic effects. For example, in a mouse model of CNS disease, 60 mg/kg of tannic acid and 200 mg/kg of sodium benzoate produced similar therapeutic effects as 1000 mg/kg of sodium benzoate alone (FIG. 2). Furthermore, tannic acid dose-dependently potentiated the effects of sodium benzoate (FIG. 2 and FIG. 3). It was observed that tannic acid alone has little or no impact on MK801-induced prepulse inhibition; however, it significantly enhanced the therapeutic effect of sodium benzoate compounds in the combined use.

Accordingly, described herein are compositions comprising a benzoate compound and an excipient, wherein the excipient is tannic acid (single species or mixture of multiple species), or a pharmaceutically acceptable salt thereof, and uses thereof for treating CNS disorders or alleviating one or more symptoms thereof. Also provided herein are co-uses of a benzoate compound and tannic acid for the intended purposes, where the benzoate compound and tannic acid may be formulated in separate compositions.

Benzoate Compound and Tannic Acid Content

The compositions described herein comprise a benzoate compound and an excipient, wherein the excipient is tannic acid, or a pharmaceutically acceptable salt thereof. The benzoate compound and tannic acid may be prepared by chemical synthesis following routine technology or obtained from a commercial vendor. Alternatively, a mixture of tannic acids may be extracted or isolated from a suitable plant source. The tannic acid extract or isolate may be subjected to one or more enrichment or purification procedures, for example, gel filtration, fractionation, and chromatography (e.g., HPLC) or a combination thereof.

A "benzoate compound" contained in any of the compositions described herein refers to a compound of the formula:

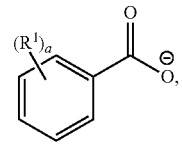

wherein $R^1$ is independently hydrogen, $C_{1-3}$ alkyl, halogen, —CN, —NO$_2$, —N$_3$, $C_2$-$C_4$ alkenyl, $C_2$-$C_4$ alkynyl, —OR, —NH$_2$, or —SR, R being hydrogen, halogen, —CN, —NO$_2$, —N$_3$, acyl, $C_{1-3}$ alkyl, $C_{2-4}$ alkenyl, $C_{2-4}$ alkynyl; and a being 0, 1, 2, 3, 4, or 5. In some embodiments, the benzoate compound, or a pharmaceutically acceptable salt thereof, is a sodium benzoate compound or lithium benzoate compound. A "sodium benzoate compound" contained in any of the compositions described herein refers to a compound of the formula:

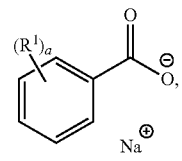

wherein $R^1$ is independently hydrogen, $C_{1-3}$ alkyl, halogen, —CN, —NO$_2$, —N$_3$, $C_2$-$C_4$ alkenyl, $C_2$-$C_4$ alkynyl, —OR, —NH$_2$, or —SR, R being hydrogen, halogen, —CN, —NO$_2$, —N$_3$, acyl, $C_{1-3}$ alkyl, $C_{2-4}$ alkenyl, $C_{2-4}$ alkynyl; and a being 0, 1, 2, 3, 4, or 5. In certain embodiments, the sodium benzoate compound is

(sodium benzoate). In certain embodiments, the lithium benzoate compound is lithium benzoate.

"$C_{1-3}$ alkyl" refers to a radical of a straight-chain or branched saturated hydrocarbon group having from 1 to 3 carbon atoms, e.g., 1 to 2 carbon atoms ("$C_{1-2}$ alkyl") or 1 carbon atom ("$C_1$ alkyl"). Unless otherwise specified, each instance of an alkyl group can be independently unsubstituted (an "unsubstituted alkyl") or substituted (a "substituted alkyl") with one or more substituents (e.g., halogen, such as F). In certain embodiments, the alkyl group is an unsubstituted $C_{1-3}$ alkyl (e.g., —CH$_3$ or —CF$_3$). "Halo" or "halogen" refers to fluorine (fluoro, —F), chlorine (chloro, —Cl), bromine (bromo, —Br), or iodine (iodo, —I).

"$C_{2-4}$ alkenyl" refers to a radical of a straight-chain or branched hydrocarbon group having from 2 to 4 carbon atoms, one or more carbon-carbon double bonds, and no triple bonds. In some examples, an $C_{2-4}$ alkenyl group has 2, 3, or 4 carbon atoms. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-4}$ alkenyl. In certain embodiments, the alkenyl group is substituted $C_{2-4}$ alkenyl, e.g., substituted with a halogen such as F or Cl, or a $C_{1-3}$ alkyl such as —$CH_3$. In an alkenyl group, a C═C double bond for which the stereochemistry is not specified (e.g., —CH═CHCH$_3$ or

)

may be an (E)- or (Z)-double bond.

"$C_{2-4}$ Alkynyl" refers to a radical of a straight-chain or branched hydrocarbon group having from 2 to 4 carbon atoms, one or more carbon-carbon triple bonds, and optionally one or more double bonds. In some embodiments, an alkynyl group has 2, 3, or 4 carbon atoms. Unless otherwise specified, each instance of an alkynyl group is independently optionally substituted, i.e., unsubstituted (an "unsubstituted alkynyl") or substituted (a "substituted alkynyl") with one or more substituents, e.g., halogen such as F or Cl, or a $C_{1-3}$ alkyl such as —$CH_3$.

Tannic acid contained in any of the compositions described herein as an excipient refers to a mixture of polygalloyl glucoses or polygalloyl quinic acid esters containing 2-12 galloyl moieties. Compositions may comprise a mixture of tannic acids having various numbers of galloyl moieties or a substantially homogeneous population of tannic acid having a defined number of galloyl moieties. Provided below is the structure of an exemplary tannic acid molecule that contains 10 galloyl moieties linked to a glucose group.

In some embodiments, the tannic acid content in the compositions disclosed herein is a mixture of tannic acids having various numbers of galloyl moieties, e.g., 2-12, or a pharmaceutically acceptable salt thereof. In some examples, the mixture of tannic acids contains tannic acids having at least 4 galloyl moieties (e.g., 4-12, 5-12, 6-12, 7-12, or 8-12 galloyl moieties) or a pharmaceutically acceptable salt thereof. Optionally, the tannic acids in the composition may be substantially free of tannic acids having 4 or less galloyl moieties. As used herein, "substantially free" of tannic acids having 4 or less galloyl moieties means that the total amount of such tannic acids in the composition is no more than 10% by weight. In some examples, the total amount of tannic acids having 4 or less galloyl moieties in the compositions described herein may be less than 8%, 5%, 2%, 1%, or less.

In other embodiments, the tannic acid content contained in the compositions described herein is a substantially homogeneous population. Such a tannic acid population may contain a tannic acid having a defined number of galloyl moieties, for example, any number between 2 and 12 (including 2 and 12), or a pharmaceutically acceptable salt thereof. As used herein, the term "substantially homogenous" means that the tannic acid having the defined number of galloyl moieties constitutes at least 85% by weight (e.g., 90%, 95%, 97%, 98%, 99%, or above) of the total tannic acid content in the composition. In some examples, the substantially homogenous tannic acid population contains tannic acids having 5, 6, 7, 8, 9, 10, 11, or 12 galloyl moieties.

The term "pharmaceutically acceptable salt" refers to those salts which are, within the scope of sound medical judgment, suitable for use in contact with the tissues of

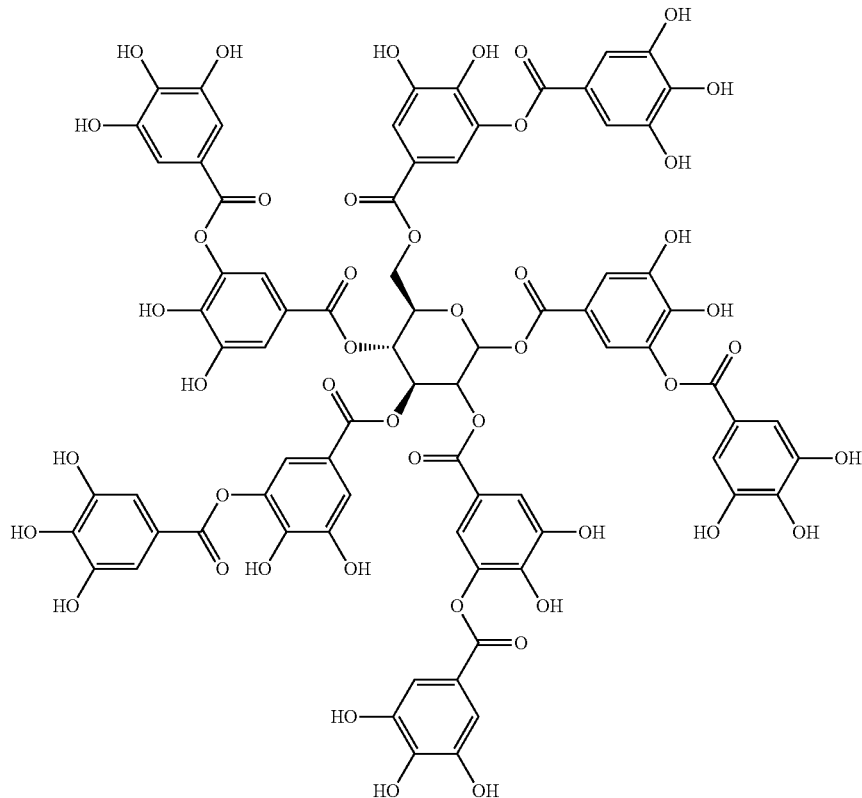 [SMILES: O=C(OC[C@H]1OC(OC(=O)c2cc(O)c(O)c(OC(=O)c3cc(O)c(O)c(O)c3)c2)C(OC(=O)c2cc(O)c(O)c(OC(=O)c3cc(O)c(O)c(O)c3)c2)[C@@H](OC(=O)c2cc(O)c(O)c(OC(=O)c3cc(O)c(O)c(O)c3)c2)[C@@H]1OC(=O)c1cc(O)c(O)c(OC(=O)c2cc(O)c(O)c(O)c2)c1)c1cc(O)c(O)c(OC(=O)c2cc(O)c(O)c(O)c2)c1]

humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference.

Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N\pm(C_{1-4} alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

In some embodiments, the benzoate compound might range from about 100 mg to 1200 mg or more in the composition and tannic acid might range from about 2.0 mg to 1200 mg or more in the composition. In some embodiments, the benzoate compound may comprise about 100 mg, about 150 mg, about 200 mg, about 300 mg, about 400 mg, about 500 mg, about 600 mg, about 700 mg, about 800 mg, about 900 mg, about 1000 mg, about 1100 mg, and about 1200 mg or more in the composition and tannic acid may comprise about 2.0 mg, about 2.5 mg, about 5 mg, about 10 mg, about 15 mg, about 20 mg, about 30 mg, about 40 mg, about 50 mg, about 60 mg, about 70 mg, about 80 mg, about 90 mg, about 100 mg, about 200 mg, about 300 mg, about 400 mg, about 500 mg, about 600 mg, about 700 mg, about 800 mg, about 900 mg, about 1000 mg, about 1100 mg, and about 1200 mg.

The ratio of the benzoate compound to tannic acid may vary. In some embodiments, the benzoate compound and tannic acid are in a ratio of 1:100 to 100:1. In some embodiments, the benzoate compound and tannic acid are in a ratio of 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, or 100:1.

Pharmaceutical Compositions

In some embodiments, the compositions comprising benzoate compound and tannic acid as described herein can be mixed with a pharmaceutically acceptable carrier to form a pharmaceutical composition, which can be used for treating any of the target diseases as described herein. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as lithium, sodium, potassium, magnesium, or calcium salts.

The pharmaceutical compositions comprising a benzoate compound and tannic acid as described herein can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In other examples, the pharmaceutical composition described herein can be formulated in sustained-release format. Suitable examples of sustained-release preparations include semipermeable matrices of solid hydrophobic polymers containing tannic acids, which matrices are in the form of shaped articles, e.g., films, or microcapsules. Examples of sustained-release matrices include polyesters, hydrogels (for example, poly(2-hydroxyethyl-methacrylate), or poly(vinyl alcohol), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The pharmaceutical compositions to be used for in vivo administration must be sterile. This is readily accomplished by, for example, filtration through sterile filtration membranes. Therapeutic compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5 .im, and have a pH in the range of 5.5 to 8.0.

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

In some embodiments, any of the pharmaceutical compositions comprising a benzoate compound and tannic acid may further comprise an additional therapeutic agent based on the intended therapeutic uses of the composition.

In some examples, the additional therapeutic agent is an agent for treating a CNS disease/disorder. Such a therapeutic agent may be an antipsychotic drug. Exemplary antipsychotic drugs include, but are not limited to, butyrophenone (e.g., Haloperidol (HALDOL™), phenothiazine (e.g., chlorpromazine (THORAZINE™), fluphenazine (PROLIXIN™), perphenazine (TRILAFON™), prochlorperazine (COMPAZINE™), thioridazine (MELLARIL™), trifluoperazine (STELAZINE™), mesoridazine, promazine, triflupromazine (VESPRIN™), levomepromazine (NOZINAN™), promethazine (PHENERGAN™), thioxanthene (e.g., chlorprothixene, flupenthixol (DEPIXOL™, FLUANXOL™), thiothixene (NAVANE™), zuclopenthixol (CLOPIXOL™, ACUPHASE™), clozapine (CLOZARIL™), olanzapine (ZYPREXA™), risperidone (RISPERDAL™, RISPERDAL CONSTA™), quetiapine (SEROQUEL™), ziprasidone (GEODON™), amisulpride (SOLIAN™), asenapine, paliperidone, Aripiprazole (ABILIFY™), dopamine partial agonists (BIFEPRUNOX™, NORCLOZAPINE™ (ACP-104)), lamotrigine (LAMICTAL™), memantine (AXURA™, AKATINOL™, NAMENDA™, EBIXA™, ABIXA™), tetrabenazine (NITOMAN™, XENAZINE™), cannabidiol, LY2140023, and the like.

Alternatively, the additional therapeutic agent can be an antidepressant and/or mood stabilizer. In certain embodiments the antidepressant comprises a monoamine oxidase inhibitor (MAOI), a tricyclic antidepressant (TCA such as IMIPRAMINE™), a tetracyclic antidepressant (TeCA), a selective serotonin reuptake inhibitor (SSRI), a noradrenergic and specific serotonergic antidepressant (NASSA), a norepinephrine (noradrenaline) reuptake inhibitor, a norepinephrine-dopamine reuptake inhibitor, and/or a serotonin-norepinephrine reuptake inhibitor (SNRI). Exemplary SSRIs include fluoxetine (PROZAC™), paroxetine (PAXIL™, SEROXAT™, escitalopram (LEXAPRO™, ESIPRAM™), citalopram (CELEXA™), sertraline (ZOLOFT™), fluvoxamine (LUVOX™)). Exemplary SNRIs include venlafaxine (EFFEXOR™), milnacipran and duloxetine (CYMBALTA™). Additional antidepressant include a noradrenergic and specific serotonergic antidepressant (NASSA) (e.g., mirtazapine (AVANZA™, ZISPIN™, REMERON™), or mianserin), a norepinephrine (noradrenaline) reuptake inhibitor (NRI) (e.g., reboxetine (EDRONAX™)), a norepinephrine-dopamine reuptake inhibitors (e.g., bupropion (WELLBUTRIN™, ZYBAN™)), Amitriptyline, Nortriptyline, Protriptyline, Desipramine, Trimipramine, Amoxapine, Bupropion, Bupropion SR, S-Citalopram, Clomipramine, Desipramine, Doxepin, Isocarboxazid, Velafaxine XR, Tranylcypromine, Trazodone, Nefazodone, Phenelzine, Lamatrogine, Lithium, Topiramate, Gabapentin, Carbamazepine, Oxcarbazepine, Valproate, Maprotiline, Mirtazapine, Brofaromine, Gepirone, Moclobemide, isoniazid, iproniazid, and the like.

In other examples, the additional therapeutic agent can be an agent for the treatment of ADD and/or ADHD. Suitable ADHD medications include, but are not limited to Statins, Amphetamine, Modafinil, Desoxyn, Methamphetamine, cocaine, arecoline, Dexmethylphenidate (Focalin, Focalin XR), dextroamphetamine (Dexedrine, Dexedrine Spansules, Dextroamphetamine ER, Dextrostat), methylphenidate (Concerta, Daytrana, Metadate CD, Metadate ER, Methylin, Methylin ER, Ritalin, Ritalin-LA, Ritalin-SR), lisdexamfetamine dimesylate (Vyvanse), mixed salts amphetamine (Adderall, Adderall XR), Atomoxetine (Strattera), clonidine hydrochloride (Catapres), guanfacine hydrochloride (Tenex), arecoline, and Pemoline.

Further, the additional therapeutic agent may be an agent for use in treating a cognitive disorder, and/or a condition characterized by neurodegeneration (e.g., Alzheimer's disease, or Parkinson's disease). Such therapeutic agents include, but are not limited to Donepezil (Aricept™), Tacrine, Rivastigmine, memantine (AXURA™, AKATINOL™, NAMENDA™, EBIXA™, ABIXA™), physostigmine, nicotine, arecoline, huperzine alpha, selegiline, Rilutek™ (riluzole), vitamine C, vitamine E, carotenoids, Ginkgo biloba extract, and the like.

Exemplary additional therapeutic agent include, but are not limited to, cariprazine, brexpiprazole, butyrophenone, phenothiazine, chlorpromazine, fluphenazine, perphenazine, prochlorperazine, thioridazine, trifluoperazine, mesoridazine, promazine, triflupromazine, levomepromazine, promethazine, thioxanthene, chlorprothixene, flupenthixol, thiothixene, zuclopenthixol, clozapine, olanzapine, risperidone, quetiapine, ziprasidone, amisulpride, asenapine, paliperidone, aripiprazole, lamotrigine, tetrabenazine, cannabidiol, LY2140023, droperidol, pimozide, butaperazine, carphenazine, remoxipride, piperacetazine, sulpiride, acamprosate, vilazodone, levomilnacipran, vortioxetine, fluoxetine, paroxetine, escitalopram, citalopram, sertraline, fluvoxamine, venlafaxine, milnacipran, duloxetine, mirtazapine, mianserin, reboxetine, bupropion, amitriptyline, nortriptyline, protriptyline, desipramine, trimipramine, amoxapine, clomipramine, desipramine, doxepin, isocarboxazid, tranylcypromine, trazodone, nefazodone, phenelzine, lamatrogine, lithium, topiramate, gabapentin, carbamazepine, oxcarbazepine, valproate, maprotiline, mirtazapine, brofaromine, gepirone, moclobemide, isoniazid, iproniazid, a statin, an amphetamine, modafinil, desoxyn, methamphetamine, cocaine, arecoline, dexmethylphenidate, dextroamphetamine, methylphenidate, lisdexamfetamine dimesylate, mixed salts amphetamine, atomoxetine, clonidine hydrochloride, guanfacine hydrochloride, arecoline, pemoline, donepezil, tacrine, rivastigmine, memantine, physostigmine, lithium salts, nicotine, huperzine alpha, selegiline, riluzole, vitamin C, vitamin E, carotenoids, and Ginkgo biloba extract.

Healthy Food Products

In some embodiments, the compositions comprising a benzoate compound and tannic acid as described herein can be a healthy food product, which can be any kinds of liquid and solid/semi-solid materials that are used for nourishing humans and animals, for improving basic behavioral functioning and/or cognitive functioning, or for facilitating treatment of any of the target diseases noted herein (e.g., a CNS disorder, including those described herein). The healthy food product may be a food product (e.g., tea-based beverages, juice, coffee, milk, jelly, cookies, cereals, chocolates, snack bars, herbal extracts, dairy products (e.g., ice cream, and yogurt)), a food/dietary supplement, or a nutraceutical formulation. The healthy food products described herein may further comprise one or more additional therapeutic agents (e.g., an additional therapeutic agent for treating a CNS disease/disorder), including those described herein.

The healthy food product described herein, containing a benzoate compound and tannic acid (e.g., sodium benzoate and tannic acid as described herein), may comprise one or more edible carriers, which confer one or more of the benefits to the tannic acids in the product as described herein. Examples of edible carriers include starch, cyclodextrin, maltodextrin, methylcellulose, carbonmethoxy cellulose, xanthan gum, and aqueous solutions thereof. Other examples include solvents, dispersion media, coatings, surfactants, antioxidants, preservatives (e.g., antibacterial agents, antifungal agents), isotonic agents, absorption delaying agents, stabilizers, gels, binders, excipients, disintegration agents, lubricants, sweetening agents, flavoring agents, dyes, such like materials and combinations thereof, as would be known to one of ordinary skill in the art. In some examples, the healthy food products described herein may further include neuroprotective foods, such as fish oil, and/or flax seed oil.

In some examples, the healthy food product is a nutraceutical composition, which refers to compositions containing components from food sources and conferring extra health benefits in addition to the basic nutritional value found in foods. A nutraceutical composition as described herein comprises the tannic acid content described herein (e.g., the tannic acid mixture or the substantially homogenous tannic acid population as described herein) and additional ingredients and supplements that promote good health and/or enhance stability and bioactivity of the tannic acids.

The actions of nutraceutical compositions may be fast or/and short-term or may help achieve long-term health objectives as those described herein, e.g., improving basic behavioral functioning and/or cognitive functioning in, e.g., human subjects who have or are at risk for diseases associated with CNS disorders. The nutraceutical compositions may be contained in an edible material, for example, as a dietary supplement or a pharmaceutical formulation. As a dietary supplement, additional nutrients, such as vitamins, minerals or amino acids may be included. The composition can also be a drink or a food product, e.g., tea, soft drink, juice, milk, coffee, cookie, cereal, chocolate, and snack bar. If desired, the composition can be sweetened by adding a sweetener such as sorbitol, maltitol, hydrogenated glucose syrup and hydrogenated starch hydrolyzate, high fructose corn syrup, cane sugar, beet sugar, pectin, or sucralose.

The nutraceutical composition disclosed herein can be in the form of a solution. For example, the nutraceutical formulation can be provided in a medium, such as a buffer, a solvent, a diluent, an inert carrier, an oil, or a creme. In some examples, the formulation is present in an aqueous solution that optionally contains a non-aqueous co-solvent, such as an alcohol. The nutraceutical composition can also be in the form of powder, paste, jelly, capsule, or tablet. Lactose and corn starch are commonly used as diluents for capsules and as carriers for tablets. Lubricating agents, such as magnesium stearate, are typically added to form tablets.

The healthy food products may be formulated for a suitable administration route, for example, oral administration. For oral administration, the composition can take the form of, for example, tablets or capsules, prepared by conventional means with acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Also included are bars and other chewable formulations.

In some examples, the healthy food product can be in a liquid form and the one or more edible carriers can be a solvent or dispersion medium comprising but not limited to, ethanol, polyol (e.g., glycerol, propylene glycol, liquid polyethylene glycol), lipids (e.g., triglycerides, vegetable oils, liposomes) or combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, it will be advisable to include an isotonic agent, such as, for example, sugars, sodium chloride or combinations thereof.

Liquid preparations for oral administration can take the form of, for example, solutions, syrups or suspensions, or they can be presented as a dry product for constitution with water or other suitable vehicle before use. In one embodiment, the liquid preparations can be formulated for administration with fruit juice. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid).

In some embodiments, the composition is a medical food. A medical food product is a food product formulated to be consumed or administered enterally. Such a food product is usually used under the supervision of a physician for the specific dietary management of a target disease, such as those described herein. In some instances, such a medical food composition is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management). In some examples, a medical food composition described herein is not one of those that would be simply recommended by a physician as part of an overall diet to manage the symptoms or reduce the risk of a disease or condition.

Any of the medical food compositions described herein, comprising benzoate compound and tannic acid and at least one carrier (e.g., those described herein), can be in the form of a liquid solution; powder, bar, wafer, a suspension in an appropriate liquid or in a suitable emulsion, as detailed below. The at least one carrier, which can be either naturally-occurring or synthetic (non-naturally occurring), would confer one or more benefits to the composition comprising a benzoate compound and tannic acid, for example, stability, bioavailability, and/or bioactivity. Any of the carriers described herein may be used for making the medical food composition. In some embodiments, the medical food composition may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents. The medical food composition may be placed in a suitable container, which may further comprise at least an additional therapeutic agent such as those described herein.

Method for Treating CNS Disorders

Another aspect of the present disclosure relates to a method for treating a central nervous system (CNS) disorder, comprising administering to a subject in need thereof a therapeutically effective amount of any of the compositions described herein. Exemplary CNS disorders include, but not limited to, attention deficit hyperactivity disorder (ADHD), schizophrenia, psychotic disorders, major depressive disorder, Alzheimer's disorder, pain, depressions, bipolar disorders, eating disorders, addiction disorders, personality disorders, tic disorders, post-traumatic stress disorder, anxiety disorders, social anxiety disorders, panic disorders, autism spectrum disorders, Asperger's disorder, Fragile X syndrome (FXS), obsessive-compulsive disorder (OCD), learning disorders, Tourette's syndrome, mild cognitive disorder (MCI), benign forgetfulness, closed head injury, dementia (e.g., vascular dementia, frontotemporal dementia, dementia with Lewy bodies, senile dementia, and mild dementia of Alzheimer), Parkinson's disorder, Huntington's disease, nocturnal enuresis, blepharospasm, non-epileptic seizure, premenstrual syndrome, and amyotrophic lateral sclerosis (ALS).

In other embodiments, the CNS disorder refers to the CNS disorders having hyperactivity symptoms. Exemplary CNS disorders having hyperactivity symptoms include, but are not limited to, schizophrenia, bipolar disorder, attention-deficit hyperactivity disorder, obsessive compulsive disorder, Tourette's syndrome, autism spectrum disorders, Fragile X syndrome, Parkinson's disease, dementia with Lewy bodies, and senile dementia.

In other embodiments, the CNS disorder refers to the CNS disorders having a sensorimotor deficit. Exemplary CNS disorders having impairs sensorimotor deficit include, but are not limited to, schizophrenia, major depressive disorder, bipolar disorder, attention deficit disorder, attention-deficit hyperactivity disorder, tic disorder, obsessive compulsive disorder, Tourette's syndrome, blepharospasm, post-traumatic stress disorder, panic disorder, Asperger's disorder, Alzheimer's disease, mild dementia of Alzheimer, dementia with Lewy bodies, Huntington's disease, personality disorders, nocturnal enuresis, and non-epileptic seizures.

In certain embodiments, the neuropsychiatric disorder is an attention deficit hyperactivity disorder including attention deficit disorder. In certain embodiments, the neuropsychiatric disorder is schizophrenia. In certain embodiments, the neuropsychiatric disorder is a psychotic disorder. In certain embodiments, the neuropsychiatric disorder is major depressive disorder. In certain embodiments, the neuropsychiatric disorder is Alzheimer's disease. In certain embodiments, the neuropsychiatric disorder is pain. In certain embodiments, the neuropsychiatric disorder is depression, including dysthymia and bereavement. In certain embodiments, the neuropsychiatric disorder is bipolar disorder including bipolar I and II disorders. In certain embodiments, the neuropsychiatric disorder is an eating disorder including bulimia and anorexia. In certain embodiments, the neuropsychiatric disorder is an addiction disorder. In certain embodiments, the neuropsychiatric disorder is a personality disorder including paranoid, schizoid, schizotypal, antisocial, borderline, histrionic, narcissistic, avoidant, dependent, and obsessive-compulsive personality disorder. In certain embodiments, the neuropsychiatric disorder is a tic disorder. In certain embodiments, the neuropsychiatric disorder is post-traumatic stress disorder. In certain embodiments, the neuropsychiatric disorder is an anxiety disorder including panic and phobic disorders. In certain embodiments, the neuropsychiatric disorder is a social anxiety disorder. In certain embodiments, the neuropsychiatric disorder is a panic disorder. In certain embodiments, the neuropsychiatric disorder is autistic spectrum disorder including Asperger's disorder. In certain embodiments, the neuropsychiatric disorder is Fragile X syndrome. In certain embodiments, the neuropsychiatric disorder is an obsessive compulsive disorder. In certain embodiments, the neuropsychiatric disorder is a learning disorder. In certain embodiments, the neuropsychiatric disorder is Tourette's syndrome. In certain embodiments, the neuropsychiatric disorder is mild cognitive impairment. In certain embodiments, the neuropsychiatric disorder is benign forgetfulness. In certain embodiments, the neuropsychiatric disorder is closed head injury. In certain embodiments, the neuropsychiatric disorder is dementia, for example, vascular dementia, frontotemporal dementia, senile dementia, mild dementia of Alzheimer, dementia with Lewy bodies, and the like. In certain embodiments, the neuropsychiatric disorder is Parkinson's disorder. In certain embodiments, the neuropsychiatric disorder is Huntington's disorder. In certain embodiments, the neuropsychiatric disorder is nocturnal enuresis. In certain embodiments, the neuropsychiatric disorder is blepharospasm. In certain embodiments, the neuropsychiatric disorder is non-epileptic seizures. In certain embodiments, the neuropsychiatric disorder is premenstrual syndrome. In certain embodiments, the neuropsychiatric disorder is amyotrophic lateral sclerosis.

In some embodiments, the subject is a human patient having or suspected of having the CNS disorder described herein.

In some embodiments, the therapeutically effective amount of the composition contains about 100 to about 1200 mg of the benzoate compound and about 2.0 to about 1200 mg of the tannic acid. In some embodiments, the therapeutically effective amount of the composition contains about 100 to about 1000 mg of the benzoate compound and about 2.5 to about 1000 mg of the tannic acid. In some embodiments, the composition comprises about 100 to about 800 mg sodium benzoate and about 20 to about 80 mg tannic acid.

In some embodiments, the composition is administered by a systemic route. In some embodiments, the systemic route is oral administration or parenteral administration.

In some embodiments, the subject is administered with the composition at a frequency of four times a day to one time a month.

In some embodiments, the subject is on another CNS disorder treatment. The therapeutic agent used in another CNS disorder treatment is selected from the additional therapeutic agent described herein.

Kits

The present disclosure also provides kits for use in improving basic behavioral functioning and/or cognitive functioning, and/or for treating a target disease as described herein (e.g., a CNS disorder). Such kits can include one or more containers comprising a composition comprising a benzoate compound and tannic acid as described herein, and optionally one or more of the additional therapeutic agents as also described herein.

In some embodiments, the kit can comprise instructions for use in accordance with any of the methods described herein. The included instructions can comprise, for example, a description of administration of the composition comprising a benzoate compound and tannic acid, and optionally a description of administration of the additional therapeutic agent(s) to improve basic behavioral functioning and/or cognitive functioning, or to treat a target disease as described herein. The kit may further comprise a description of selecting an individual suitable for treatment based on identifying whether that individual has the disease or is at risk for the disease. In still other embodiments, the instructions comprise a description of administering two or more agents of the disclosure to an individual at risk of the disease or in need of improving basic behavioral functioning and/or cognitive functioning.

The instructions relating to the use of the composition comprising a benzoate compound and tannic acid to achieve the intended therapeutic effects generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert may indicate that the composition is used for the intended therapeutic utilities. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Kits may optionally provide additional components such as buffers and interpretive information. Normally, the kit comprises a container and a label or package insert(s) on or associated with the container. In some embodiments, the invention provides articles of manufacture comprising contents of the kits described above.

Applications of Compositions Comprising a Benzoate Compound and Tannic Acid

The present disclosure provides methods of treating, reducing the risk, or delaying the onset for a CNS disorder, in a subject in need thereof, the methods comprising administering to the subject an effective amount (e.g., therapeutically effective amount) of a composition comprising a benzoate compound (e.g., lithium benzoate or sodium benzoate) and an excipient, wherein the excipient is tannic acid, or a pharmaceutically acceptable salt thereof.

As used herein, the term "treating" refers to the application or administration of a composition including one or more active agents to a subject, who is in need of the treatment, for example, having a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

To achieve any of the intended therapeutic effects described herein, an effective amount of a composition comprising a benzoate compound and tannic acid, or a pharmaceutically acceptable salt thereof may be administered to a subject in need of the treatment via a suitable route.

The terms "subject," "individual," and "patient" are used interchangeably herein and refer to a mammal being assessed for treatment and/or being treated. Subjects may be human, but also include other mammals, particularly those mammals useful as laboratory models for human disease, e.g., mouse, rat, rabbit, dog, etc.

A human subject who needs the treatment may be a human patient having, at risk for, or suspected of having a target CNS disease/disorder. A subject having a target disease or disorder can be identified by routine medical examination, e.g., laboratory tests, organ functional tests, and/or behavior tests. A subject suspected of having any of such target disease/disorder might show one or more symptoms of the disease/disorder. A subject at risk for the disease/disorder can be a subject having one or more of the risk factors for that disease/disorder, for example, a genetic factor. In some instances, the human subject is a child who has, is suspected of having, or is at risk for a CNS disorder associated with children, for example, attention deficit/hyperactivity disorder (ADHD), autism, learning disorder, and Asperger's disorder.

A human subject who needs the treatment may be a human patient that has been treated, or is currently being treated for a CNS disease/disorder. For example, a subject may have been treated or is currently being treated for schizophrenia and may be treated for schizophrenia using the compositions described herein. In another example, a subject may have been treated or is currently being treated for Alzheimer's disorder and may be treated for Alzheimer's disorder using the compositions described herein. A subject that has been treated for a CNS disease/disorder can be a subject that was treated prior to the treatment described herein (e.g., two weeks, one month, one year, or more prior to treatment as described herein) and may no longer on the treatment at the time the treatment method described herein is applied to the subject. A subject that has been treated for a CNS disease/disorder can be a subject that was treated once, twice, or more prior to treatment as described herein. A subject that is currently being treated for a CNS disease/disorder is a subject that is still on such a treatment when the treatment method described herein is applied to the subject.

The methods and compositions described herein may be used to treat a CNS disorder, including, but not limited to, CNS disorders having hyperactivity symptoms, and CNS disorders having impairs sensorimotor deficit. Exemplary CNS disorders that can be treated by the methods and compositions described herein include attention deficit hyperactivity disorder (ADHD), schizophrenia, psychotic disorders, major depressive disorder, Alzheimer's disorder, pain, depressions, bipolar disorders, eating disorders, addiction disorders, personality disorders, tic disorders, post-traumatic stress disorder, anxiety disorders, social anxiety disorders, panic disorders, autism spectrum disorders, Asperger's disorder, Fragile X syndrome (FXS), obsessive-compulsive disorder (OCD), learning disorders, Tourette's syndrome, mild cognitive disorder (MCI), benign forgetfulness, closed head injury, dementia (e.g., vascular dementia, frontotemporal dementia, mild dementia of Alzheimer, dementia with Lewy bodies (DLB), senile dementia and the like), Parkinson's disorder, Huntington's disease, nocturnal enuresis, blepharospasm, non-epileptic seizure, premenstrual syndrome, and amyotrophic lateral sclerosis (ALS).

Exemplary CNS disorders having hyperactivity symptoms include, but not limited to, schizophrenia, bipolar disorder, attention-deficit hyperactivity disorder, obsessive compulsive disorder, Tourette's syndrome, autism spectrum disorders, Fragile X syndrome, Parkinson's disease, dementia with Lewy bodies, and senile dementia.

Exemplary CNS disorders having a sensorimotor deficit include, but not limited to, schizophrenia, major depressive disorder, bipolar disorder, attention deficit disorder, attention-deficit hyperactivity disorder, tic disorder, obsessive compulsive disorder, Tourette's syndrome, blepharospasm, post-traumatic stress disorder, panic disorder, Asperger's disorder, Alzheimer's disease, mild dementia of Alzheimer, dementia with Lewy bodies, Huntington's disease, personality disorders, nocturnal enuresis, and non-epileptic seizures.

As used herein, the term "personality disorders" refers to mental disorders characterized by enduring maladaptive patterns of behavior, cognition, and inner experience, exhibited across many contexts and deviating markedly from those accepted by the individual's culture. These patterns develop early, are inflexible, and are associated with significant distress or disability. For example, the personality disorders can include, but not limited to, paranoid, schizoid, schizotypal, antisocial, borderline, histrionic, narcissistic, avoidant, dependent, and obsessive-compulsive personality disorder.

A "therapeutically effective amount" of a composition comprising a benzoate compound and tannic acid described herein is an amount sufficient to provide a therapeutic benefit in the treatment of a condition or to delay or minimize one or more symptoms associated with the condition. A therapeutically effective amount of a composition comprising a benzoate compound and tannic acid means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

As used herein, "an effective amount" refers to the amount of each active agent (e.g., the benzoate compound and the tannic acid as described herein) required to confer therapeutic effect on the subject, either alone or in combination with one or more other active agents, such as one or more of the additional therapeutic agents described herein. In some embodiments, the therapeutic effect is improvement of NMDA receptor functioning, and/or improvement of basic behavioral functioning, and/or improvement of cognitive functioning. In some embodiments, the therapeutic effect is alleviating one or more symptoms associated with any of the CNS disorders described herein.

Determination of whether an amount of the composition as described herein achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder. Alternatively, sustained continuous release formulations of a composition as described herein may be appropriate. Various formulations and devices for achieving sustained release are known in the art.

Generally, for administration of any of the compositions, an exemplary daily dosage of the compositions provided herein might range from about 100 mg to 1200 mg or more of the benzoate compound and about 2.0 mg to 1200 mg or more of tannic acid, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering one or more initial doses at a suitable interval over a suitable period. If necessary, multiple maintenance doses can be given to the subject at a suitable interval over a suitable period of time. However, other dosage regimens may be useful, depending on the pattern of pharmacokinetic decay that the practitioner wishes to achieve. For example, dosing from one to four times a day or as long as a month is contemplated. In some embodiments, dosing ranging from about 100 mg to about 1200 mg of a benzoate compound (such as about 100 mg, about 150 mg, about 200 mg, about 300 mg, about 400 mg, about 500 mg, about 600 mg, about 700 mg, about 800 mg, about 900 mg, about 1000 mg, about 1100 mg, and about 1200 mg) and about 2.0 mg to about 1200 mg of tannic acid (such as about 2.0 mg, about 2.5 mg, about 5 mg, about 10 mg, about 15 mg, about 20 mg, about 30 mg, about 40 mg, about 50 mg, about 60 mg, about 70 mg, about 80 mg, about 90 mg, about 100 mg, about 200 mg, about 300 mg, about 400 mg, about 500 mg, about 600 mg, about 700 mg, about 800 mg, about 900 mg, about 1000 mg, about 1100 mg, and about 1200 mg) may be used. In some embodiments, dosing frequency can be once a day, twice a day, once every other day, once every week, once every 2 weeks, or once every 4 weeks. The dosing regimen can vary over time.

In some embodiments, for an adult patient of normal weight, doses ranging from about 100 to about 1200 mg of a benzoate compound and about 2.0 to about 1200 mg of tannic acid may be administered. In some embodiments, for an adult patient of normal weight, doses ranging from about 100 to about 1000 mg of the benzoate compound and about 2.5 to about 1000 mg of the tannic acid. In some embodiments, for an adult patient of normal weight, doses ranging from about 100 mg/kg to 500 mg/kg of a benzoate compound and about 5 mg/kg to 50 mg/kg of tannic acid may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of composition comprising a benzoate compound and a tannic acid as described herein will depend on the specific benzoate compound, tannic acid, or tannic acid mixture, and/or other active ingredient employed, the type and severity of the disease/disorder, whether the composition is administered for preventive or therapeutic purposes, previous therapy, the patient's clinical history and response to the antagonist, and the discretion of the attending physician. Typically, the clinician will administer a composition, until a dosage is reached that achieves the desired result.

Conventional methods, known to those of ordinary skill in the art of medicine, can be used to administer the composition (e.g., a pharmaceutical composition or a nutraceutical composition) to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularlly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing a benzoate compound and tannic acid and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of benzoate compound or tannic acid, can be dissolved and administered in a pharmaceutical excipient such as Water-for-Injection, 0.9% saline, or 5% glucose solution.

In one embodiment, a composition comprising a benzoate compound and tannic acid is administered via a site-specific or targeted local delivery technique. Examples of site-specific or targeted local delivery techniques include various implantable depot sources of the compositions or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Also within the scope of the present disclosure are the combined uses of a benzoate compound as described herein and tannic acid for treating a CNS disorder or alleviating a symptom thereof. The benzoate compound and tannic acid may be formulated in separate compositions and may be administered to a subject in need sequentially or concurrently, e.g., at the doses of the benzoate compound and tannic acid and/or the benzoate compound/tannic acid ratios as described herein.

Treatment efficacy for a target disease/disorder can be assessed by methods well-known in the art.

Combined Therapy

Also provided herein are combined therapies using any of the compositions comprising a benzoate compound and tannic acid described herein and an additional therapeutic agent, such as those described herein. The term combination therapy, as used herein, embraces administration of these agents (e.g., a composition comprising a benzoate compound and tannic acid and an anti-CNS agent) in a sequential manner, that is, wherein each therapeutic agent is administered at a different time, as well as administration of these therapeutic agents, or at least two of the agents, in a substantially simultaneous manner. Sequential or substantially simultaneous administration of each agent can be affected by any appropriate route including, but not limited to, oral routes, intravenous routes, intramuscular, subcutaneous routes, and direct absorption through mucous membrane tissues. The agents can be administered by the same route or by different routes. For example, a first agent (e.g., a composition comprising a benzoate compound and tannic acid) can be administered orally, and an additional agent (e.g., an anti-CNS agent) can be administered intravenously.

As used herein, the term "sequential" means, unless otherwise specified, characterized by a regular sequence or order, e.g., if a dosage regimen includes the administration of a composition comprising a benzoate compound and tannic acid and an anti-CNS agent, a sequential dosage regimen could include administration of the composition comprising a benzoate compound and tannic acid before, simultaneously, substantially simultaneously, or after administration of the anti-CNS agent, but both agents will be administered in a regular sequence or order. The term "separate" means, unless otherwise specified, to keep apart one from the other. The term "simultaneously" means, unless otherwise specified, happening or done at the same time, i.e., the agents of the invention are administered at the same time. The term "substantially simultaneously" means that the agents are administered within minutes of each other (e.g., within 10 minutes of each other) and intends to embrace joint administration as well as consecutive administration, but if the administration is consecutive it is separated in time for only a short period (e.g., the time it would take a medical practitioner to administer two agents separately). As used herein, concurrent administration and substantially simultaneous administration are used interchangeably. Sequential administration refers to temporally separated administration of the agents described herein.

Combination therapy can also embrace the administration of the agents described herein (e.g., a composition comprising a benzoate compound and tannic acid and an anti-CNS agent) in further combination with other biologically active ingredients (e.g., a different anti-CNS agent) and non-drug therapies (e.g., surgery).

It should be appreciated that any combination of a composition comprising a benzoate compound and tannic acid and an additional therapeutic agent (e.g., an anti-CNS agent) may be used in any sequence for treating a target disease. The combinations described herein may be selected on the basis of a number of factors, which include but are not limited to the effectiveness of increasing NMDA receptor functioning, improving basic behavioral functioning, enhancing cognitive functioning, and/or alleviating at least one symptom associated with the target disease, or the effectiveness for mitigating the side effects of another agent of the combination. For example, a combined therapy described herein may reduce any of the side effects associated with each individual members of the combination, for example, a side effect associated with the additional therapeutic agent.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Current protocol in Neuroscience (Developmental Editor: Eric Prager, Online ISBN: 9780471142300, DOI: 10.1002/0471142301). Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The specific embodiments provided herein are, therefore, to be construed as merely illustrative, and not limitative of the remainder of the disclosure in any way whatsoever. All publications cited herein are incorporated by reference for the purposes or subject matter referenced herein.

EXAMPLES

In order that the present disclosure may be more fully understood, the following examples are set forth. The examples described in this application are offered to illustrate compositions comprising combinations of sodium benzoate and tannic acid and uses thereof are not to be construed in any way as limiting their scope.

Example 1: Rescue/Protective Effects of Combinations of Tannic Acid and Benzoate Compounds on MK801-Treated Mice The objective of this experiment was to assess the potential mechanisms of action of compositions comprising a sodium benzoate and tannic acid in alleviating symptoms of CNS disorders, using a mouse model having such symptoms induced by MK801, a well-known NMDA receptor antagonist (Kovacic et al., Oxid Med Cell Longev, 3(1):13-22 [2010]). MK801 was known to induce NMDA receptor hypofunction and consequently MK801 and compositions comprising sodium benzoate and/or tannic acid were administrated in mice by intraperitoneal (i.p.) injections or via the oral route before the behavioral tests (i.e., open field and prepulse inhibition), respectively.

NMDA receptor hypofunction induced by MK801 produces symptoms of central nerve system diseases, including stereotypic behaviors, anhedonia, learning and memory deficits, working memory impairment and sensorimotor function abnormalities (Furuya et al., Eur J Pharmacol, 364(2-3):133-140 [1999]; McLamb et al., Pharmacol Biochem Behav, 37(1):41-45 [1990]; Vardigan et al., Pharmacol Biochem Behav, 95(2):223-229 [2010]; White et al., Pharmacol Biochem Behav, 59(3):613-617 [1998]; Wu et al., Psychopharmacology (Berl), 177(3):256-263 [2005]). Such symptoms are associated with various CNS disorders, including attention deficit hyperactivity disorder (ADHD), schizophrenia, psychotic disorders, major depressive disorder, Alzheimer's disorder, pain, depressions, bipolar disorders, eating disorders, addiction disorders, personality disorders, tic disorders, post-traumatic stress disorder, anxiety disorders, social anxiety disorders, panic disorders, autism spectrum disorders, Asperger's disorder, Fragile X syndrome (FXS), obsessive-compulsive disorder (OCD), learning disorders, Tourette's syndrome, mild cognitive disorder (MCI), benign forgetfulness, closed head injury, dementia (e.g., vascular dementia, frontotemporal dementia, dementia with Lewy bodies, senile dementia, and mild dementia of Alzheimer), Parkinson's disorder, Huntington's disease, nocturnal enuresis, blepharospasm, non-epileptic seizure, premenstrual syndrome, and amyotrophic lateral sclerosis (ALS).

Figure 1:
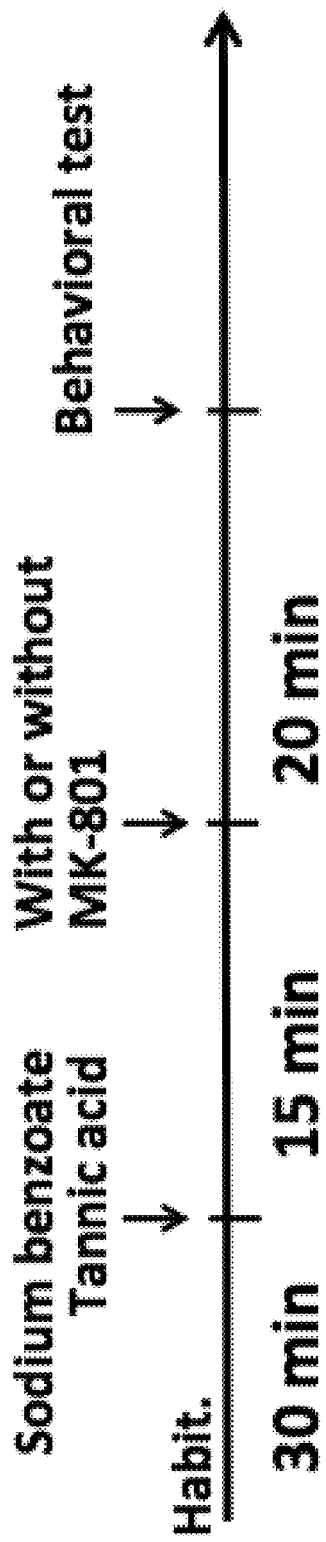
FIG. 1 is a diagram showing an exemplary experimental design. Sodium benzoate or tannic acid alone, combinations of sodium benzoate and tannic acid, or the control vehicle were administrated to each mouse by oral gavage 15 minutes prior to MK801 injection. Intraperitoneal injections of MK801 were administered to each mouse 20 minutes prior to the behavior tests.

The exemplary experimental design is illustrated in FIG. 1.

Materials and Methods
Animal and Housing Conditions

C57BL/6J male mice were group housed (3-5 mice per cage) with food and water available ad libitum in polysulfone ventilated cages (Alternative Design, AR, USA) in the animal rooms. The colony was maintained on a 12/12-h light/dark cycle at the temperature of 22±2° C. and all behavioral studies will be performed during the dark cycle. All animals used in this study were adult mice (at least 2.5 months of age).

Drug Administration
Cohort 1

The mice were randomly assigned into six groups listed below:
Group 1: Vehicle+Saline control
Group 2: Vehicle+MK801
Group 3: Sodium benzoate (1000 mg/kg)+MK801
Group 4: Sodium benzoate (200 mg/kg)+MK801
Group 5: Sodium benzoate (200 mg/kg)+Tannic Acid (30 mg/kg)+MK801
Group 6: Sodium benzoate (200 mg/kg)+Tannic Acid (60 mg/kg)+MK801.

Each mouse in Groups 2-6 received an acute administration of MK801 dissolved in normal saline (0.1 mg/kg, i.p.) 20 minutes prior to the behavioral tests. Each mouse in Groups 3-6 received an acute administration of sodium benzoate or sodium benzoate in combination with tannic acid (dissolved in PBS, 30 or 60 mg/kg) via oral gavage 20 minutes prior to the MK801 administration.

Cohort 2

The mice were randomly assigned into ten groups listed below:
Group 7: Vehicle+Saline control
Group 8: Vehicle+MK801
Group 9: Sodium benzoate (1000 mg/kg)+MK801
Group 10: Sodium benzoate (200 mg/kg)+MK801
Group 11: Sodium benzoate (600 mg/kg)+MK801
Group 12: Sodium benzoate (200 mg/kg)+Tannic Acid (30 mg/kg)+MK801
Group 13: Sodium benzoate (200 mg/kg)+Tannic Acid (60 mg/kg)+MK801
Group 14: Sodium benzoate (600 mg/kg)+Tannic Acid (10 mg/kg)+MK801
Group 15: Sodium benzoate (600 mg/kg)+Tannic Acid (30 mg/kg)+MK801
Group 16: Sodium benzoate (600 mg/kg)+Tannic Acid (60 mg/kg)+MK801.

Each mouse in Groups 8-16 received an acute administration of MK801 dissolved in normal saline (0.1 mg/kg, i.p.) 20 minutes prior to the behavioral tests. Each mouse in Groups 9-16 received an acute administration of sodium benzoate or sodium benzoate in combination with tannic acid (dissolved in PBS, 10, 30 or 60 mg/kg) via oral gavage 20 minutes prior to the MK801 administration.

Cohort 3

The mice were randomly assigned into five groups listed below:
Group 17: PBS+Saline control
Group 18: PBS+MK801
Group 19: Tannic acid_10 mg/kg+MK801
Group 20: Tannic acid_30 mg/kg+MK801
Group 21: Tannic acid_100 mg/kg+MK801.

Each mouse in Groups 18-21 received an acute administration of MK-801 (a NMDA receptor antagonist, dissolved in normal saline (0.1 mg/kg, i.p.) 20 minutes prior to behavioral tests. On the other hand, each mouse in Groups 19-21 received an acute administration of tannic acid (dissolved in 30% PEG400 in PBS, 10, 30 or 100 mg/kg) via oral gavage 20 minutes prior to the MK801 administration.

Examination of the Effects of Administrations of Combinations of Sodium Benzoate and Tannic Acid on MK801 Treated Mice All mice of cohort 1 in this study were assessed with open field test as described herein. The mice of cohorts 2 and 3 in this study were assessed with prepulse inhibition test as described herein.

Spontaneous Locomotor Activity Determined by Open Field Test

The open field test is a common measurement of novelty induced exploratory behavior and general activity in both mice and rats. In this study, mice were placed in a Plexiglas cage (37.5 cm×21.5 cm×18 cm) under 50-65 lux light intensity. Their spontaneous locomotor activities were measured for 60 minutes using the EthoVision video tracking system (Noldus Information Technology, the Netherlands). The travel distance of each mouse was measured as an index of locomotion activity. It generates hyperactivity which is frequently applied as animal models including, but not limited to, schizophrenia, bipolar disorder, attention-deficit hyperactivity disorder, obsessive compulsive disorder, Tourette's syndrome, autism spectrum disorders, Fragile X syndrome, Parkinson's disease, dementia with Lewy bodies, and senile dementia (see Rubia et al., 2010; Sheppard and Bradshaw, 1999; Bent et al., 2014; Powell and Miyakawa, 2006; Nestler and Hyman, 2010; Bubeni´kova´-Vales̆ova et al., 2008; Gobira et al., 2013; Lai et al., 2014; Maio et al., 2014; Sontag et al., 2010; Ding et al., 2014; Walitza et al., 2007; Finestone et al., 1982; Golimstok et al., 2011).

Sensorimotor Function Determined by Prepulse Inhibitor Test

Pre-attentive processes tend to be automatic and rapid, and to operate outside of conscious awareness, whereas deliberate attention processes have limited resources, require more efforts, and operate more slowly. A common measure of pre-attentive process is prepulse inhibition. This paradigm has been commonly examined in mouse models of several mental illnesses, including, but not limited to, schizophrenia, major depressive disorder, bipolar disorder, attention deficit disorder, attention-deficit hyperactivity disorder, tic disorder, obsessive compulsive disorder, Tourette's syndrome, blepharospasm, post-traumatic stress disorder, panic disorder, Asperger's disorder, Alzheimer's disease, mild dementia of Alzheimer, dementia with Lewy bodies, Huntington's disease, personality disorders, nocturnal enuresis, and non-epileptic seizures (see McAlonan et al., 2002; Braff et al., 2001; Giakoumaki et al., 2007; Ueki et al., 2006; Perriol et al., 2005; Ludewig et al., 2002; Castellanos et al., 1996; Cadenhead et al., 2000; Matsuo et al., 2017; Lai et al., 2014; McCool et al., 2003; Arguello & Gogos, 2006) because the deficit manifests in a similar manner to the human symptom.

Prepulse inhibition was used as an index of sensorimotor gating function using SR-LAB startle apparatus (San Diego Instruments, San Diego, Calif., USA). The startle stimulus was a 40 ms, 120 dB white noise burst. In the pre-pulse (pp)+pulse trials, a 20 ms white noise pre-pulse stimuli of 82 dB (pp10) or 90 dB (pp18) was presented 100 ms before a 40 ms 120 dB pulse. The trials were presented pseudo-randomly and separated by inter-trial interval of 15 s on average (varying between 10 to 20 s) under 72 dB background noise. The percentage of pre-pulse inhibition was evaluated by the following formula: % PPI=100×[(PA score)−(pp-P score)]/(PA score), where the PA score was the average of the PA value in the middle blocks.

Results

The Effects of Combinations of Sodium Benzoate and Tannic Acid on Locomotion of MK801 Treated Mice In this example, the open field test was used to investigate the effects of combining sodium benzoate and tannic acid on the general motility of mice of cohort 1 with MK801-induced hyper-locomotion. Administration of sodium benzoate at doses of 1000 mg/kg rescued/protected mice from MK801 induced hyper-locomotion more than 200 mg/kg (FIG. 2). Administration of sodium benzoate at a dose of 200 mg/kg in combination with tannic acid at a dose of 60 mg/kg produced a pronounced rescuing effects similar as 1000 mg/kg of sodium benzoate alone (FIG. 2). Therefore, the data demonstrated that tannic acid potentiates the rescuing/protective effect of sodium benzoate on MK801 induced hyper-locomotion in mice.

The Effects of Combinations of Sodium Benzoate and Tannic Acid on Sensorimotor Gating Function of MK801 Treated Mice In this example, the prepulse inhibition test was used to investigate the effects of combining sodium benzoate and tannic acid on sensorimotor function of MK801-treated mice of cohort 2. 200 mg/kg or 600 mg/kg sodium benzoate alone did not show much effects on rescuing MK801-disrupted PPI. As compared to the groups treated with 1000 mg/kg sodium benzoate alone, increasing doses of tannic acid 30, 60 mg/kg and 10, 30, 60 mg/kg respectively for 200 mg/kg and 600 mg/kg groups displayed significantly higher percentages of prepulse inhibition (FIG. 3). Similar results were obtained with prepulse intensities of 82 dB and 90 dB (FIG. 3). Further, it was observed that tannic acid alone showed little or no effect on rescuing MK801-induced hyper-locomotion in mice. See discussions below. Therefore, the data demonstrated that tannic acid dose-dependently potentiates the rescuing/protective effect of sodium benzoate on MK801-induced prepulse inhibition deficits in mice.

Figure 4:
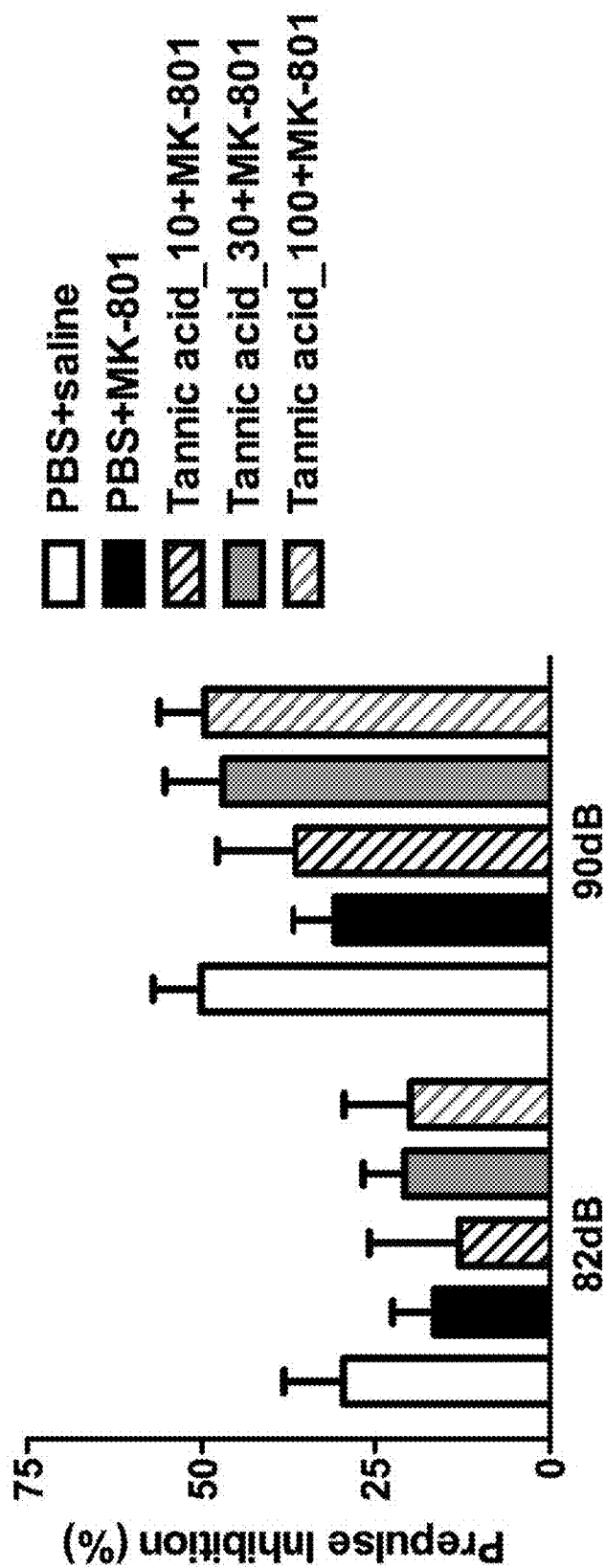
FIG. 4 is a chart showing that tannic acid alone has little or no improvement of MK-801-induced prepulse inhibition.

The Effects of Tannic Acid on Sensorimotor Gating Function of MK801 Treated Mice In this example, the prepulse inhibition test was used to investigate the effects of tannic acid on sensorimotor gating function of MK801-treated mice of cohort 3. 10, 30, 100 mg/kg of tannic acid treatment showed little or no effects on MK801-disrupted PPI. Similar results were obtained with prepulse intensities of 82 dB and 90 dB (FIG. 4). Therefore, the data demonstrated that tannic acid does not have the rescuing/protective effect on MK801-induced prepulse inhibition deficits in mice.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A composition, comprising a benzoate compound and an excipient, wherein the excipient comprises tannic acid, or a pharmaceutically acceptable salt thereof, wherein the benzoate compound and the tannic acid are at a ratio of 100:1 to 1:100 by weight in the composition, and wherein tannic acids having 5-12 galloyl moieties constitutes at least 85% by weight of the total tannic acids in the composition.

2. The composition of claim 1, wherein the benzoate compound is a sodium benzoate compound or a lithium benzoate compound.

3. The composition of claim 2, wherein the sodium benzoate compound is sodium benzoate and the lithium benzoate compound is lithium benzoate.

4. The composition of claim 1, wherein the benzoate compound is about 100 to about 1,200 mg in the composition and the tannic acid is about 2.0 to about 1,200 mg in the composition.

5. The composition of claim 4, wherein the benzoate compound is about 100 to about 500 mg in the composition and the tannic acid is about 2.5 mg to 500 mg in the composition.

6. The composition of claim 1, wherein the benzoate compound and the tannic acid are at a ratio of 1:1 to 100:1 by weight in the composition.

7. The composition of claim 1, further comprising an additional therapeutic agent for a central nervous system (CNS) disorder.

8. The composition of claim 7, wherein the additional therapeutic agent for the CNS disorder is selected from the group consisting of cariprazine, brexpiprazole, butyrophenone, phenothiazine, fluphenazine, perphenazine, prochlorperazine, thioridazine, trifluoperazine, mesoridazine, promazine, triflupromazine, promethazine, thioxanthene, chlorprothixene, flupenthixol, thiothixene, clozapine, olanzapine, risperidone, quetiapine, ziprasidone, amisulpride, asenapine, paliperidone, aripiprazole, lamotrigine, droperidol, pimozide, butaperazine, carphenazine, remoxipride, piperacetazine, sulpiride, acamprosate, tetrabenazine, vilazodone, levomilnacipran, fluoxetine, paroxetine, escitalopram, citalopram, sertraline, fluvoxamine, venlafaxine, milnacipram, duloxetine, mirtazapine, mianserin, reboxetine, bupropion, amitriptyline, nortriptyline, protriptyline, desipramine, trimipramine, amoxapine, clomipramine, doxepin, tranylcypromine, selegiline, trazodone, nefazodone, phenelzine, lamotrogine, lithium salts, topiramate, gabapentin, carbamazepine, oxcarbazepine, valporate, maprotiline, mirtazapine, brofaromine, moclobemide, isoniazid, iproniazid, amphetamine, mixed salts amphetamine, modafinil, desoxyn, methamphetamine, cocaine, arecoline, dexmethylphenidate, dextroamphetamine, methylphenidate, lisdexamfetamine dimesylate, atomoxetine, clonidine, guanfacine, arecoline, pemoline, donepezil, tacrine, rivastigmine, memantine, physostigmine, selegiline, riluzole, tannic acid, and Ginkgo Biloba extract.

9. The composition of claim 1, wherein the composition is formulated for oral administration or parenteral administration.

10. The composition of claim 9, wherein the composition is a tablet, a capsule, a soft chew, or a gel.

11. The composition of claim 1, wherein the composition is a pharmaceutical composition, which further comprises a pharmaceutically acceptable carrier.

12. The composition of claim 1, wherein the composition is a nutraceutical composition, a medical food, or a health food.

13. The composition of claim 1, wherein the tannic acid comprises 6-12 galloyl moieties.

14. The composition of claim 1, wherein the tannic acid is a substantially homogenous population of tannic acid molecules having 5, 6, 7, 8, 9, 10, 11, or 12 galloyl moieties.

15. The composition of claim 1, wherein the tannic acid is a mixture of tannic acid molecules having different numbers of galloyl moieties ranging from 5-12.

16. The composition of claim 1, wherein tannic acids having 4 or less galloyl moieties is less than 8% by weight of the total amount of the tannic acids in the composition.

17. A method for reducing hyperactivity or rescuing sensorimotor deficit in a subject having or suspected of having a central nervous system (CNS) disorder, the method comprising administering to the subject a therapeutically effective amount of the composition of claim 1.

18. The method of claim 17, wherein the CNS disorder is selected from the group consisting of attention deficit hyperactivity disorder, schizophrenia, major depressive disorder, Alzheimer's disorder, bipolar disorders, personality disorders, tic disorders, post-traumatic stress disorder, panic disorders, autism spectrum disorders, Asperger's disorder, Fragile X syndrome, obsessive-compulsive disorder, Tourette's syndrome, dementia, Parkinson's disorder, Huntington's disease, nocturnal enuresis, blepharospasm, and non-epileptic seizure.

19. The method of claim 18, wherein the CNS disorder is a CNS disorder having hyperactivity symptoms selected from the group consisting of schizophrenia, bipolar disorder, attention-deficit hyperactivity disorder, obsessive compulsive disorder, Tourette's syndrome, autism spectrum disorders, Fragile X syndrome, anxiety disorder, psychotic disorder, Parkinson's disease, dementia with Lewy bodies, and senile dementia.

20. The method of claim 18, wherein the CNS disorder is a CNS disorder having sensorimotor deficit selected from the group consisting of schizophrenia, major depressive disorder, bipolar disorder, learning disorder, attention deficit disorder, attention-deficit hyperactivity disorder, tic disorder, obsessive compulsive disorder, Tourette's syndrome, blepharospasm, post-traumatic stress disorder, panic disorder, Asperger's disorder, Alzheimer's disease, mild dementia of Alzheimer, dementia with Lewy bodies, mild cognitive impairment, frontotemporal dementia, vascular dementia, benign forgetfulness, Huntington's disease, personality disorders, nocturnal enuresis, and non-epileptic seizures.

21. The method of claim 18, wherein the subject is a human patient having the CNS disorder.

22. The method of claim 17, wherein the therapeutically effective amount of the composition contains about 100 to about 1200 mg of the benzoate compound and about 2 to about 1200 mg of the tannic acid.

23. The method of claim 22, wherein the therapeutically effective amount of the composition contains about 100 to about 500 mg of the benzoate compound and about 2.5 to about 500 mg of the tannic acid.

24. The method of claim 17, wherein the composition is administered to the subject by a systemic route.

25. The method of claim 24, wherein the systemic route is oral administration or parenteral administration.

26. The method of claim 17, wherein the subject is administered the composition four times per day to one time per month.

27. The method of claim 17, wherein the subject is on another treatment of the CNS disorder.

* * * * *